United States Patent [19]
Vahlensieck et al.

[11] Patent Number: 6,153,374
[45] Date of Patent: Nov. 28, 2000

[54] METHOD FOR IDENTIFYING INHIBITORS OF SORAPHEN A RESISTANT ACETYL-COENZYME A CARBOXYLASE

[75] Inventors: Hans-Friedrich Vahlensieck, Basel, Switzerland; Albert Hinnen, Jena, Germany

[73] Assignee: Novartis Finance Corporation, New York, N.Y.

[21] Appl. No.: 08/469,708

[22] Filed: Jun. 6, 1995

Related U.S. Application Data

[62] Division of application No. 08/354,973, Dec. 13, 1994, Pat. No. 5,641,666.

[51] Int. Cl.[7] ............................... C12Q 1/00; C12Q 1/18
[52] U.S. Cl. ................................. 435/4; 435/29; 435/32; 435/69.2
[58] Field of Search .................................... 435/4, 15, 29, 435/32, 69.2; 424/9.2; 514/432, 450

[56] References Cited

PUBLICATIONS

Al–Feel, W., et al., "Cloning of the Yeast FAS3 Gene and Primary Structure of Yeast Acetyl–CoA Carboxylase", *PNAS*, 89:4534–4538 (1992).

Klebe, R.J., et al., "A General Method for Polyethylene–glycol–induced Genetic Transformation of Bacteria and Yeast", *Gene*, 25:333–341 (1983).

Matsuhashi, M., "Acetyl–CoA Carboxylast from Yeast", *Methods in Enzymology*, Lowenstein, J.M., Ed., 14:3–8 (1969).

Roessler, P.G., "Genetic engineering approaches for enchanced production of biodiesel fuel from microalagae", *Abstr. Pap. Am. Chem. Soc.*, 205 Meet., Pt. 2:BTEC29 (1993).

Sikorski, R.S., et al., "A System of Shuttle Vectors and Yeast Host Designed for Efficient Manipulation of DNA in *Saccharomyces cerevisiae*", *Genetics*, 122:19–27 (1989).

Vahlensieck, H–F., Ph.D. Thesis, "A Genetic Approach to Determine the Biochemical Targert of the Antimicrobial Agent, Soraphen A", Philosophisch–Naturwissenschaftlichen Fakultät der Universität Basel (1993).

Vahlensieck H., Idenfication of the Yeast ACC1 Gene Product as the Target of the Polyketide Fungicide Soraphen A, Current Genetics 25, 95–100, 1994.

Beforf, N., Isolation and Structure Elucidation of Soraphen A, A Novel Antifungal Macrolide from Soragnium cellulosum, Liebigs Ann Chem 1017–1021, 1993.

*Primary Examiner*—Ralph Gitomer
*Attorney, Agent, or Firm*—Larry W. Stults

[57] ABSTRACT

An assay to identify inhibitors of soraphen A resistant acetyl-coenzyme A carboxylase comprising measuring the reactivity of acetyl-coenzyme A carboxylase in the presence and in the absence of a compound suspected to inhibit soraphen A resistant acetyl-coenzyme A carboxylase reactivity, and comparing the reactivity measurements to identify inhibitors of soraphen A resistant acetyl-coenzyme A carboxylase.

2 Claims, No Drawings

METHOD FOR IDENTIFYING INHIBITORS OF SORAPHEN A RESISTANT ACETYL-COENZYME A CARBOXYLASE

This is a divisional application of application Ser. No. 08/354,973, filed Dec. 13, 1994 now U.S. Pat. No. 5,641,666.

The present invention relates to genes encoding an acetyl-coenzyme A carboxylase resistant to soraphen A inhibition, methods of isolating these genes, purified acetyl-coenzyme A carboxylase resistant to soraphen A inhibition and assays to identify inhibitors of soraphen A resistant acetyl-coenzyme A (acetyl-CoA) carboxylase.

The 18-membered macrolide soraphen A, is a secondary metabolite of the myxobacterium *Sorangium cellulosum*, strain So ce 26. The chemical structure of Soraphen A is shown in formula (I).

(I)

[Chemical structure of Soraphen A]

Until now over 60 natural variants of soraphen A could be isolated (Augustiniak et al, 'Chemische Arbeiten', in: 'Wissenschaftlicher Ergebnisbericht', Seiten 36–40, GBF Braunschweig, 1989). Soraphen A exhibits strong activity as a fungicide, while it is without effect on bacteria. In one instance it was shown to interfere with acetyl-CoA carboxylase (Pridzun, 'Untersuchungen zum Wirkungsmechanismus von Soraphen A', Technische Universität Braunschweig, Germany, doctoral thesis) which is a key enzyme in fatty acid biosynthesis.

The main objective of the present invention is to provide soraphen A resistant genes which genes are able to confer soraphen A resistance to a host organism comprising said genes. It has now surprisingly been found that all soraphen A resistant genes so far isolated in yeast, a model system for fungi, are mutated in a single gene. The gene is identified to be yeast acetyl-CoA carboxylase the DNA sequence of which is known (Al-Feel et al, Proc. Natl. Acad. Sci. USA 89:4534–4538, 1992). Thus yeast strains resistant to soraphen A surprisingly result from mutation of a single gene, namely acetyl-CoA carboxylase. The mutations show dominant, semidominant, or recessive phenotypes in heterozygous diploid strains.

The mutant genes according to the invention can be used to produce recombinant soraphen A resistant acetyl-CoA carboxylase, which in turn can be used in in vitro assays to determine the inhibitory effect of soraphen A derivatives or other compounds on the activity of the mutant acetyl-CoA carboxylase. These assays allow to identify improved soraphen A derivatives which induce less fungi resistant to soraphen A or compounds which are useful in anti-resistance strategies.

The present invention relates primarily to a DNA molecule comprising a gene encoding acetyl-CoA carboxylase resistant to soraphen A inhibition, but especially to a molecule comprising a gene encoding fungal, preferably yeast acetyl-CoA carboxylase.

Acetyl-CoA carboxylase catalyzes the committed step in fatty acid biosynthesis, yielding malonyl-CoA, the donor of the two-carbon units for the synthesis of long-chain fatty acids. In higher and lower eucaryotes the enzyme is a multifunctional polypeptide forming tetramers comprising domains for biotin binding, biotin carboxylation, and transcarboxylation. The yeast, chicken and rat carboxylases have an overall sequence identity of 34%.

Yeast acetyl-CoA carboxylase has a calculated molecular weight of about 250 kD and consists of about 2200 amino acids. The nucleotide sequence of the gene was determined by Al-Feel et al, Proc. Natl. Acad. Sci. USA 89:4534–4538, 1992. The biotin binding site and the biotin carboxylase domains are comprised by the N-terminal half of the yeast protein whereas the transcarboxylase domain is comprised by the C-terminal half.

It has now been found that mutations confering soraphen A resistance are preferably located in the N-terminal half of the yeast acetyl-CoA carboxylase. Within the N-terminal half mutations and preferably dominant mutations in the biotin carboxylase domain are preferred which are assumed to block the enzymes ability to carboxylate biotin. The present invention thus primarily relates to genes encoding acetyl-CoA carboxylase resistant to soraphen A inhibition which comprise a mutation of the gene, and especially a mutation in the biotin carboxylase domain. Alternatively, mutations are preferred which inhibit tetramer formation.

Mutations confering soraphen A resistance to acetyl-CoA carboxylase and preferably to yeast acetyl-CoA carboxylase can be dominant or recessive, and they can be single or multiple point mutations, deletion or insertion mutations. Preferably the mutations are point mutations altering a codon which encodes an amino acid selected from the group consisting of unpolar (glycine, alanine, valine, leucine, isoleucine, phenylalanine, proline), polar (serine, threonine, cytosine, methionine, tryptophan, tyrosine, asparagine, glutamine), basic (lysine, arginine, Histidine), and acidic amino acids (aspartic acid, glutamic acid). Codons which are preferred targets of mutation are codons which encode an amino acid selected from the group consisting of valine, serine, threonine, histidine, and lysine. Among the codons for polar amino acids, mutations are preferred which inhibit phosphorylation or dephosphorylation of the protein.

In a preferred embodiment of the invention the mutation is selected from the group consisting of mutations changing valine at amino acid position 50 to phenylalanine, histidine at amino acid position 53 to arginine, lysine at amino acid position 73 to arginine, and serine at amino acid position 77 to tyrosine. Most preferred is the mutation changing serine at amino acid position 77 to tyrosine.

Another object of the present invention is to provide methods of isolating a gene encoding fungal acetyl-CoA carboxylase resistant to soraphen A inhibition. In one embodiment of the invention the method comprises (a) selecting and isolating a fungal strain, and preferably a yeast strain, resistant to soraphen A;

(b) purifying restriction fragments of cDNA or genomic DNA of said resistant strain;

(c) cloning the restriction fragments in bacteria;

(d) probing the clones for the presence of restriction fragments obtainable from the gene encoding wild-type acetyl-coenzyme A carboxylase;

(e) isolating and sequencing the gene encoding soraphen A resistant acetyl-CoA carboxylase; and (f) identifying the mutation or the mutations.

To select for example soraphen A resistant yeast strains, within a preferred embodiment of the invention $10^4$ to $10^{10}$ and preferably $10^6$ to $10^9$ yeast cells are plated on a solidified medium containing 0.1 to 50 μg/ml and preferably 1 to 10 μg/ml soraphen A. Mating of the resulting yeast strains, zygote isolation, sporulation and tetrad analysis can be performed as described by Guthrie and Fink, 'Guide to Yeast Genetics and Molecular Biology' in: 'Methods of Enzymology', volume 194, 1991. Spore viability from crosses involving acetyl-CoA carboxylase mutants can be increased by feeding the spores with a drop of YPD-FA. After further cultivation mutant strains are used to purify restriction fragments of cDNA or genomic DNA which result from complete or partial restriction digestion. The preparation of genomic DNA or of RNA from yeast and the synthesis of cDNA from the RNA constitute techniques well known in yeast gene technology. Restriction digestion of DNA is done according to the manufacturers' instructions supplied with the restriction enzymes. Preferably the restriction fragments result from restriction digestion using restriction enzymes which are known not to cut within the gene encoding wildtype acetyl-CoA carboxylase such as for exapmle SacI. The purified restriction fragments are then spliced into known selectible DNA vector molecules and the resultant plasmids are used to transform bacteria such as E. coli, Bacillus or Streptomyces. Clonal colonies derived after transformation and selection with antibiotics such as neomycin, ampicillin, kanamycin or tetramycin are probed by colony hybridization for restriction fragments obtainable from genes encoding wild-type acetyl-CoA carboxylase. Techniques for probing bacterial colonies are described in detail in Sambrook et al, Molecular Cloning: A Laboratory Manual, Cold Spring Harbor Laboratory Press, Cold Spring Harbor, N.Y., 1989, the relevant parts of which are herein incorporated by reference. Bacterial clones harbouring such DNA molecules are isolated, their plasmid DNA is prepared and the gene encoding soraphen A resistant acetyl-CoA carboxylase is sequenced. Optionally the isolated DNA molecules can be transformed into yeast before sequencing to test whether they are able to confer soraphen A resistance. The sequence obtained is compared to the sequence of the wild-type gene and mutations are identified. To avoid sequencing of the complete gene to identify the mutation confering soraphen A resistance, it is also possible to shuffle restriction fragments between the wild-type and the mutant genes using techniques of recombinant DNA known in the art The chimaeric genes can be tested whether they are able to confer soraphen A resistance or not by transformation in yeast. This allows to narrow down the DNA region responsible for resistance.

The methods examplfied above for yeast can accordingly be applied to alternative fungi, from which strains resistant to soraphen A inhibition can be isolated.

The soraphen A resistant genes obtained by this method can be dominant, semidominant, or recessive.

A different method of isolating a gene encoding fungal acetyl-CoA carboxylase resistant to soraphen A inhibition, comprises (a) selecting and isolating a fungal strain, and preferably a yeast strain, resistant to soraphen A;

(b) purifying restriction fragments of cDNA or genomic DNA of said resistant strain;

(c) cloning the restriction fragments in the fungus by complementation;

(d) isolating soraphen A resistant transformants;

(e) isolating and sequencing the gene encoding soraphen A resistant acetyl-CoA carboxylase; and (f) identifying the mutation or the mutations.

To clone a restriction fragment in a fungus but especially in yeast by complementation the restriction fragment either comprises the whole gene encoding acetyl-CoA carboxylase including promoter and termination signals, or the known wild-type sequence of the acetyl-CoA carboxylase gene is used to select a specific restriction fragment of the gene which allows splicing of the fragment inbetween promoter and termination sequences active in the fungus, but especially in yeast. The purified restriction fragments are spliced into known DNA vector molecules which preferably contain a marker gene selectible in yeast and the resultant plasmids are used to transform strains with a defective acetyl-CoA carboxylase. These strains are auxotrophic for fatty acids and can be grown in media supplemented with fatty acids. Preferably, media are supplemented with 0.005% to 1% and more preferably with 0.01% to 0,1% palmitic acid. Strains which have been transformed with a gene encoding acetyl-CoA carboxylase resistant to soraphen A are no more auxotrophic for fatty acids and can be grown on medium which is not supplemented with for example palmitic acid. Optionally they can be identified by expression of a marker gene selectible in yeast. The soraphen A resistant genes obtained by this method can be dominant, semidominant, or recessive. Preferably the method is used to obtain dominant alleles.

Yet another method of isolating a gene encoding fungal acetyl-CoA carboxylase resistant to soraphen A inhibition, comprises (a) selecting and isolating a fungal strain, and preferably a yeast strain, resistant to soraphen A;

(b) preparing cDNA or genomic DNA from the resistant strain;

(c) using said DNA as template for polymerase chain reaction amplification with primers complementary to sequences of the wild-type acetyl-CoA carboxylase gene;

(d) isolating and sequencing the amplification products; and (e) identifying the mutation or the mutations.

Polymerase chain reaction amplification can be done as described in Saiki et al, Science 239:487–491, 1988. In this in vitro process there are used chemically synthesised oligonucleotides of 10 bp to 40 bp, and preferably of 20 bp to 30 bp length complementary to sequences of the wild-type acetyl-CoA carboxylase gene, which are designed to make up the ends of the DNA sequence to be amplified. Under suitable conditions, hybridization of the oligonucleotides with the complementary regions on the target DNA single strands produced by denaturing occurs. The double-stranded regions produced in this manner are used as primers for the subsequent polymerase reaction and the process steps of denaturation, hybridization of the oligonucleotides and synthesis of DNA are repeated 15 to 40 and preferably 20 to 30 times. In this process there may be used in addition to DNA polymerases from *E. coli* especially heat-stable polymerases from thermophilic bacteria, for example *Thermus aquaticus*.

Amplification products are identified after gel electrophoresis and can be sequenced either directly or after splicing into DNA vector molecules and cloning in microorganisms such as *E. coli*. Normally the mutated acetyl-CoA carboxylase is not amplified as a single fragment but as several overlapping fragments. Therefore, the method can also be used to selectively isolate acetyl-CoA carboxylase gene sequences supposed to be mutated in soraphen A resistant genes.

The present invention also relates to a purified fungal acetyl-CoA carboxylase, but especially to a purified yeast acetyl-CoA carboxylase resistant to soraphen A inhibition and to a method of purifying said acetyl-CoA carboxylase resistant to soraphen A inhibition, comprising (a) homogenization of fungal cells; and (b) avidin affinity chromatography of protein.

For protein purification fungal cells are harvested by centrifugation and subsequently homogenized in a suitable buffer containing protease inhibitors. It is preferable to remove cell debris by centrifugation and/or ultracentrifugation and to precipitate protein using for example ammoniumsulfate. Ultimately protein is applied on an avidin-agarose gel column and eluted. The fractions giving the highest extinctions at 280 nm are pooled For storing the purified protein it is possible to precipitate the combined fractions for example by ammonium sulfate and to redissolve the protein in buffer containing glycerol which can then be stored −70° C.

Once having identified and isolated genes encoding soraphen A resistant acetyl-CoA carboxylase a purified protein can be obtained from transgenic heterologous expression of said DNA, i.e., placing a recombinant DNA comprising a DNA sequence coding for a protein exhibiting acetyl-CoA carboxylase activity into an appropriate bacterial, yeast or other cell expression system. A method of producing purified recombinant fungal acetyl-CoA carboxylase resistant to soraphen A, comprises the steps of (a) transforming a host organism with recombinant DNA encoding soraphen A resistant fungal acetyl-CoA carboxylase; and (b) isolating the protein from the host organism or its culture supernatant Suitable hosts include bacteria such as *E. coli* and Bacillus. Other suitable expression system hosts include insect cells grown in culture. These insect cells may be infected with a baculovirus containing a recombinant DNA molecule according to the invention.

Alternatively, the baculovirus may be used to infect a living insect, and the insect cells used as an expression system host. The expression system host is then allowed to produce an expression supernatant. This allows facile generation of large amounts of purified recombinant acetyl-CoA carboxylase by isolating the enzyme from the expression supernatant.

Purified acetyl-CoA carboxylase can then be used in an assay to identify inhibitors of soraphen A resistant acetyl-CoA carboxylase, comprising (a) incubating a first sample of soraphen A resistant acetyl-CoA carboxylase and its substrate;

(b) measuring the reactivity of the acetyl-CoA carboxylase in step (a);

(c) incubating a second sample of soraphen A resistant acetyl-CoA carboxylase and its substrate in the presence of a sample comprising a compound suspected to inhibit the enzyme's reactivity;

(d) measuring the reactivity of the acetyl-CoA carboxylase in step (c); and (e) comparing the reactivities of acetyl-CoA carboxylase in steps (a) and (c).

Suitable acetyl-CoA carboxylase for the above assay can be obtained using the purification methods of the present invention. Suitable substrates are acetyl-CoA or structural analogs that are capable of being carboxylated by the enzyme and $HCO_3^-$ with the preferred substrate being acetyl-CoA and $NaHCO_3$. Preferably acetyl-CoA is at a concentration of about 0.1 mM to 10 mM, more preferably at at about 0.1 mM to 1 mM, and most preferably at about 0.5 M.

In addition to the acetyl-CoA carboxylase and a suitable substrate, the reaction mixture can contain a suitable buffer, suitable cofactors and suitable divalent cations as cofactors. A suitable buffer includes any suitable biological buffer that can provide buffering capability at a pH conductive to the reaction requirements of the enzyme. Preferably the buffer provides buffering capability in the pH range 7 to 9, more preferably in the pH range 7.5 to 8.5, and most preferably at a pH of about 8.0, e.g. 50 mM Tris-HCl at pH 8.0. A preferred cofactor for acetyl-CoA carboxylase is ATP, preferably at a concentration of about 0.5 nM to about 100 nM, more preferably at about 3.75 nM. Preferably the divalent cation is a divalent metal cation, more preferably magnesium. Additional components of the reaction mixture can be for example BSA and EDTA. The reaction is carried out at a suitable temperature to allow the reaction to proceed. Such a suitable temperature is about 4° C. to about 40° C., more preferably from about room temperature to about 35° C., and most preferably at about 30° C. The most preferred reaction mixture contains 50 mM Tris-HCl pH 8.0, 10 mM $MgCl_2$, 7,5 g/l BSA, 3.75 nM ATP, 10 mM EDTA, $^{14}C$-labeled $NaHCO_3$ (10 $\mu$Ci per sample with a specific activity of 52.4 $\mu$Ci/$\mu$mol) and different amounts of acetyl-CoA carboxylase. Preferably the reaction is started with the addition of acetyl-CoA.

Uninhibited reactivity of the acetyl-CoA carboxylase is any measure of enzymatic activity of acetyl-CoA carboxylase while in the presence of suitable substrate only. Measures of enzymatic activity are generally know to those of skill in the art, including equilibrium constants, reaction velocities of the appearance of reaction products or the consumption of reaction substrates, reaction kinetics, thermodynamics of the reaction, spectrophotometric analysis of reaction products, detection of labeled reaction components, etc. See, generally, Segel, 'Biochemical Calculations', 2nd edition, John Wiley and Sons, New York (1976); Suelter, 'A Practigal Guide to Enzymology', John Wiley and Sons, New York (1985). The preferred method of measuring the enzymatic activity is to determine the amount of incorporated $^{14}C$ from $^{14}C$-labeled $NaHCO_3$ by scintillation.

Suitable inhibitor compounds are identified using the above methods. Inhibited reactivity is determined in the same manner as uninhibited reactivity but with the addition of an inhibitor of acetyl-CoA carboxylase. The concentration of the inhibitor may vary depending on the inhibitory activity, but generally it will be in an amount ranging from about 10 nM to about 200 mM, more preferably about 0.1 mM to about 100 mM, and most preferably about 1 mM to about 10 mM. Generally, the acetyl-CoA or other substrate will be added to a mixture containig the enzyme and inhibitor and then an enzyme activity will be determined as described previously.

Comparing the inhibited reactivity to the uninhibited reactivity of the acetyl-CoA carboxylase includes determining whether a significant decrease in enzyme activity is observed in the inhibited reactivity compared to the uninhibited reactivity. A significant decrease is a decrease in enzymatic activity that is larger than the margin of error inherent in the measurement technique, preferably a decrease by about 50% of the activity in the absence of the inhibitor, more preferably a decrease by about 90%, and most preferably a decrease to a level of enzymatic activity that is essentially undetectable.

Another assay to identify inhibitors of soraphen A resistant fungal acetyl-CoA carboxylase comprises (a) growing a first culture of a fingus resistant to soraphen A and recording the growth curve;

(b) growing a second culture of the fungus resistant to soraphen A in the presence of a sample comprising a compound suspected to inhibit the reactivity of soraphen A resistant acetyl-CoA carboxylase and recording the growth curve; and (c) comparing the growth curves recorded in steps (a) and (b).

To record the growth curve of a culture of for example yeast the culture medium is inoculated at a concentration of $10^4$ to $10^8$ and preferably $10^6$ to $10^7$ yeast cells per liter. Then the culture is grown at a temperature between 20° C. and 40° C., preferably at about 30° C. under continuous agitation. At intervals samples are withdrawn and their optical density is determined. Preferably the optical density is measured at 600 nm ($OD_{600}$). The values of the $OD_{600}$ correlate with cell density and are plotted against time measured from the starting point of the culture. Alternatively, aliquots of the culture are removed and the cell number is determined by counting under the microscope. The growth curves recorded in the presence of a compound suspected to inhibit acetyl-CoA carboxylase are compared to the growth curves recorded in the absence of an inhibitory compound. The compound is considered to exert a significant inhibitory effect if the slope of the growth curve of the inhibited culture is reduced by more than 50%, preferably more than 80% and most preferably more than 95% compared to the uninhibited culture.

The invention will be further described by reference to the following examples. These examples are provided for purposes of illustration only, and are not intended to be limiting unless otherwise specified.

EXAMPLES

Example 1

Media and strains 1.1. Media

The basic culture medium is YPD containing 1% Bacto-yeast extract (Difco), 2% Bacto-peptone (Difco) and 2% glucose (Merck).

YPD-SOR-10 is YPD medium supplemented with 10 μg/ml soraphen A.

YPD-FA is YPD supplemented with fatty acid (0.03% palmitic acid, Fluka) and 1% Tween 40 (Fluka).

The synthetic minimal medium SDHL contains 0.67% yeast Nitrogen Base without amino acids (Difco), amino acids as required, and 2% glucose. SDHLS medium is used for yeast transformations by electroporation and is SDHL supplemented with 1 M sorbitol.

For plates the media are solidified with 2% Bacto-Agar (Difco).

1.2. Strains

*Saccharomyces cerevisiae* strain YS 18 (MATα; his 3-11, 3-15; leu 2-3, 2-112; ura 3-Δ5; can$^R$; cir$^+$) is chosen as the wild-type. YHV 18 (MATa; his 3-11, 3-15; leu 2-3, 2-112; ura 3-Δ5; can$^R$; cir$^+$) is isolated after a mating type switch of YS 18 and is therefore isogenic.

Example 2

Mating-type switch

YS 18 is transformed with plasmid pGAL-HO, containing the gene for the mating-type sequence-specific endonuclease HO under the control of the GAL promoter and the URA3 marker gene, according to the method of Klebe (Klebe et al, Gene 25:333–341, 1983). PGAL-HO was kindly provided by Dr. P. Lindner, Biocenter, Basel, Switzerland. The HO gene is switched on by growing the transformants for 2 hours on complete medium containing 2% galactose instead of glucose. The culture is plated on YPD plates and screened for "a" mating type colonies using an appropriate 'α' tester strain. Next the pGAL-HO plasmid is aborted using 5-fluoro-orotic acid (Pharmacia). Plasmid loss is confirmned by Southern analysis or PCR. After crosses with tester strains, about 80% of the cells sporulate after 3 days; spore viability is greater than 95%.

Example 3

Isolation of mutants

Each of the isogenic strains YS 18 and YHV 18 is grown in 5 ml of YPD to late exponential phase. The culture is diluted $10^4$ fold to give culture A the viable cell number of which is determined. Twenty tubes each containing 5 ml of YPD are inoculated with 10 μl of culture A, which corresponds to about 10 cells, and are incubated at 28° C. until a density of $10^7$ cells/ml is attained. 1 ml aliquots of each of the tubes are plated on YPD-SOR-10 and the plates are incubated at 30° C. for 3 days. To ensure isolation of independent mutants from each of the 20 YPD-SOR-10 plates only colonies with different shape or sizes are selected. Mutant colonies are restreaked twice on YPD before storing them as glycerol stock cultures at −70° C.

To exclude the presence of soraphen A resistant mutants at the beginning of the cultivation of culture A, the remainder of culture A is plated on YPD-SOR-10 and incubated at 30° C. for 3 days. No growth of colonies is observed.

52 independent mutants are isolated using this protocol. 8 mutants of each mating type (YCI101, YCI103, YCI105, YCI115, YCI119, YCI126, YCI138, and YCI141 derived from YHV 18 and YCI1, YCI2, YCI10, YCI16, YCI37, YCI39, YCI43, and YCI51 derived from YS 18) which show rigorous growth are selected for further analysis.

In a first step all of the mutants are backcrossed with the wild-type stain of the opposite mating type, the diploid strains are sporulated and the asci are subjected to tetrad analysis. From each cross at least six complete tetrads are examined and all of them are found to segregate 2:2 for soraphen A resistance and soraphen A sensitivity. This indicates mutations at a single genetic locus.

In another step the MIC of the diploids from the backcrosses is determined. None of the diploids is as sensitive to soraphen A as the wild-type strain. Instead, a variety of semidominant or dominant phenotypes is found with a MIC ranging from 0.35 μg/ml to 54 μg/ml.

Finally 8 mutants of one mating type are crossed against one mutant of the other mating type. After sporulation and tetrad analysis all 4 spores of each tetrad are soraphen A resistant. No gene conversion is observed as expected with low numbers of tetrads. At least six complete tetrads from each cross are checked. The results indicate that all mutations map to the same genetic locus.

Example 4

Growth curves 100 ml YPD medium in a 500 ml flask is inoculated with about $10^7$ YS 18 yeast cells/ml and incubated for growth at 180 rpm at 30° C. Before the addition of soraphen A at time point 0, the cells have already been incubated for 1 hour. The control is treated identically, but receives no soraphen A. Total cell numers are monitored by measuring the $OD_{600}$. The number of viable cells called the titer is determined by plating on YPD plates. The number of soraphen A resistant cells is counted by plating on YPD-SOR plates containing the same soraphen A concentration as in the flask.

In the presence of soraphen A a complete inhibition of growth is observed for approximately 40 hours; thereafter growth recovers due to soraphen A resistant mutants. The viable cell counts reveal that during the first 20 hours extensive cell killing occurs. The minimal inhibitory concentration (MIC) as determined from the growth curves is 0.1 μg/ml.

Example 5
Determination of the minimal inhibitory concentration (MIC)

Yeast colonies are grown for 2 days at 30° C. on a YPD plate and replica pated on a set of YPD-SOR plates. The following soraphen A concentrations are used: 0 μg/ml, 0.35 μg/ml, 0.76 μg/ml, 1.5 μg/ml, 3.13 μg/ml 6.7 μg/ml, 15.45 μg/ml and 54.5 μg/ml. After growth for 24 hours at 30° C. the plates are inspected for growth.

Using this method the MIC for diploids from the backcrosses of soraphen A resistant yeast strains are determined to range from 0.35 μg/ml to 54 μg/ml.

Example 6
Cloning techniques

Restriction enzyme digestions and ligation reactions are performed as described in Maniatis et al, 'Molecular Cloning: A Laboratory Manual', Cold Spring Harbor Laboratory Press, 1989. Dephosphorylated cloning vector is prepared in the following way: 10 μl vector DNA (about 1 μg/μl), 2 μl restriction enzyme, 2 μl 10× restricition buffer and 6 μl of water are incubated at 37° C. for 2 hours. Then an additional 2 μl of restriction enzyme is added, and the sample incubated at 37° C. for 2 more hours. 3 μl bovine alkaline phosphatase (150 units/μl, Gibco BRL, Maryland, USA), 3 μl 10× dephosphorylation buffer (0.5 M Tris-HCl pH 8, 0,5 M NaCl) and 2 μl water are added and the tubes incubated for 1 hour at 65° C. The linearized and dephosphorylated vector is purified on a 0.7% TAE agarose gel. The DNA is then isolated from the gel slice using the gene clean kit (BIO101, California, USA).

E. coli is transformed by electroporation (Dower et al, Nucleic Acid Res. 16:6127–6145) and plasmid DNA from E. coli is isolated using the Qiagen Midiprep Kit (Qiagen Inc., California, USA) or the Magic Miniprep Kit (Promega, Wisconsin, USA).

Example 7

Preparation and screening of a gene bank for acetyl-CoA carboxylase in E. coli 40 μg chromosomal DNA of the mutant strain is digested with 50 units of SacI for 1 hour at 37° C. After 1 hour another 50 units of restriction enzyme are added and the incubation is continued for another hour. The digested DNA is electrophoresed on an 0.8% TAE gel, and fragments of 7.5 kb to 9 kb are isolated. The DNA fragments are cloned into the dephophorylated SacI site of pBlueKS+ (Stratagene) and transformed into E. coli. The resulting transformants are screened by colony hybridization probing with DNA comprising the known acetyl-CoA carboxylase wild-type gene.

Example 8
Colony hybridization

A DIG-labeled SacI restriction fragment containing the whole acetyl-CoA carboxylase coding region is prepared with the DIG Labeling Kit (Böhringer Mannheim) according to the protocols of the manufacturer. Colonies are replica plated onto commercially available nylon filters allowing 5 minutes of contact. The filters are then placed onto Whatman 3M filter paper and soaked with the following solutions one after the other: 0.5 M NaOH (5 min); 1 M Tris-HCl pH 7.5 (2×1 min); 0.5 M Tris-HCl pH 7.5 (1 min); and 1.5 M NaCl (5 min). After air drying the filters are crosslinked for 3 minutes with UV light of 254 nm. Hybridization of filters and detection of positive colonies is performed using the DIG Luminescence Detection Kit (Böhringer Mannheim). The most stringent wash of the filters is performed in 0.1% SDS and 0.1× SSC at 58° C.

After screening of the gene banks prepared as described in example 7 seven clones were obtained: pCI2 (YCI2), pCI10 (YCI10), pCI39 (YCI39), pCI43 (YCI43), pCI101 (YCI101), pCI138 (YCI138), pCI141 (YCI141)

Example 9

Preparation and screening of a gene bank for acetyl-CoA carboxylase in yeast 40 μg genomic DNA of the mutant strain is digested with 0.8 units BamHI for 25 minutes (experimentally determined) at 37° C. The partially digested DNA is electrophoresed on an 0.8% agarose gel, and fragments of 6 kb to 10 kb are isolated. The DNA fragments are cloned into BamHI-cut and dephophorylated pRS316 (CEN6, ARSH4, URA3, Amp$^r$, ori; Sikorski et al, Genetics 122:19–27, 1989) and transformed into E. coli. The resulting transformatns are devided into 10 pools each containing about 1000 single clones. Each clone pool is propagated once in 100 ml of LB medium containing 100 μg/ml ampicillin and plasmid DNA is prepared. The gene bank is screened by transforming yeast YS 18 with a fixed amount of DNA from each pool. The resulting SDHLS plates are replica plated twice on YPD-SOR-10. In order to avoid the selection of secondary soraphen A mutations, only the colonies that show resistance on both soraphen A containing plates are isolated from the SDHLS plates.

Using this method the acetyl-CoA carboxylase gene of the mutant YCI37 strain is isolated. The gene is able to restore soraphen A resistance to wild-type strains upon transformation.

Example 10
Yeast transformation using electroporation 5 ml of an overnight culture are diluted in 95 ml of YPD and grown for about 3 hours on a shaker with 180 rpm at 30° C. All the following steps are done at 4° C. or on ice. The culture is divided into two tubes and centrifuged for 5 minutes at 3000 rpm. The cells are washed 3 times in 50 ml of sterile water and once in 20 ml of 1 M sorbitol. Finally the cells are resuspended in 200 μl of sterile 1 M sorbitol and transformed in a 0.4 cm gap cuvette at 2.5 kV, 200 Ohm and 25 μF after mixing 40 μl of cells with up to 5 μg of DNA in up to 5 μl of sterile water. After the pulse the cells are immediately diluted with 1 ml 1 M ice cold sorbitol. 100 μl to 1 ml of the cells are plated on SDHLS agar and incubated at 30° C. for 2–3 days.

Example 12
Restriction fragment shuffling

Several restriction fragments are shuffled between the wild-type acetyl-CoA carboxylase gene pCI18 obtained from YS 18 and the mutant gene pCI101. Resulting constructs are transformed into YS 18 and checked for their ability to confer soraphen A resistance. Based on the data, the mutation of pCI101 is mapped to the 1.9 kb SacI/NheI fragment comprising the N-terminal part of acetyl-CoA carboxylase and its promoter.

Example 13
DNA sequencing

DNA is sequenced using the dideoxy chain-termination method of Sanger et al, Procl. Natl. Acad Sci. USA 74:5463–5467, 1977, using double-stranded plasmid DNA as a template. The oligonucleotide primers are synthesized on an Applied Biosystems Model 380A Synthesizer.

The complete DNA sequence of the 1.9 kb DNA fragment shown in example 11 to be responsible for soraphen A resistance conferred by pCI101 is sequenced. It is found that a single base change results in the substitution of serine by a tyrosine residue at amino acid position 77. The same mutation is found for the acetyl-CoA carboxylase gene of the mutant YCI37 yeast strain. pCI141 also comprises this mutation but in addition contains mutations changing valine at amino acid position 50 to phenylalanine and histidine at amino acid position 53 to arginine. The mutations found in pCI43 change valine at amino acid position 50 to phenylalanine and lysine at amino acid position 73 to arginine. For pCI39 mutations have been found to change histidine at amino acid position 53 to arginine and threonine at amino acid position 57 to alanine.

Example 14
Purification of acetyl-CoA carboxylase acetyl-CoA carboxylase is enriched from 15l of cells grown overnight in YPD medium at 30° C. using avidin-affinity chromatography. Cells are harvested by centrifugation and suspended in isolation buffer (200 mM potassium phosphate buffer pH 6.5; 5 mM β-mercaptoethanol; 1 mM EDTA; 100 g/l glycerol; 200 $\mu$M PMSF; 1 $\mu$M leupeptin; 1 $\mu$M pepstatin A; 0.66 $\mu$M antipain; 0.5 $\mu$M trypsin inhibitor (soybean); 200 $\mu$M TPCK; 100 $\mu$M TLCK) to give a final volume of 300 ml. Then 520 ml glassbeads (0.25–0.5 mm diameter) are added and the cells are homogenized in a bead mill for 5 minutes. Cell debris is removed by centirfugation, and the supernatant is filtered through glass wool preceding ultracentrifugation at 100 000 g at 4° C. After ultracentrifugation the supernatant is again filtered through glasswool and then 243 g/l ammoniumsulfate are added slowly to precipitate the proteins. Precipitated proteins are pelleted and resuspended in 24 ml column loading buffer (200 mM potassium phosphate buffer pH 6.5; 15 mM β-mercaptoethanol; 1 mM EDTA; 500 mM KCl; 3.1 mM $Na_3N$; 100 g/l glycerol; 200 $\mu$M PMSF; 1 $\mu$M leupeptin; 1 $\mu$M pepstatin A; 0.66 $\mu$M antipain; 0.5 $\mu$M trypsin inhibitor (soybean); 200 $\mu$M TPCK, 100 $\mu$M TLCK). The sample is applied on a C16 column (16 mm diameter) loaded with 10 ml monomeric avidin-agarose gel equilibrated with column loading buffer. The flow rate used is 1 ml/minute. Then the column is washed with column loading buffer until the $OD_{280}$ of the eluate is below 0.01. The fractions giving the highest extinctions at 280 nm are combined and protein is precipitated by slow addition of 243 g/l ammonium sulfate. The precipitated protein is pelleted, washed with ammonium sulfate-saturated loading buffer and then resuspended in 3 ml storage buffer (200 mM potassium phosphate buffer pH 6.5; 5 mM β-mercaptoethanol; 200 g/l glycerol). Aliquoted enzyme solutions are stored at −70° C. Protein concentrations are determined according to Bradford (Bradford, Anal. Biochem 72:248–254, 1976).

Example 15
Enzymatic assay of acetyl-CoA carboxylase

Assays of enzymatic activity in the enriched fractions of wild-type and mutant strains can be performed in two different ways:

15.1. Incorporation of radioactively labeled hydrogencarbonate

In one method incorporated $HCO_3^-$ is distinguished from unincorporated $HCO_3^-$ by the different stability of $HCO_3^-$ and malonyl-coenzyme A in acidic solutions. $HCO_3$ is acid label and is removed by heating the samples to 60° C. in a continous flow of nitrogen. Remaining radioactivity is present as malonyl-coenzyme A and is quantified to determine acetyl-CoA activity.

For the assay the following components are combined in a glass tube: 50 mM Tris-HCl pH 8, 10 mM MgCl, 7.5 g/l BSA (fatty acid free), 3,75 nM ATP, 10 mM EDTA, 10 $\mu$l (wild-type) or 25 $\mu$l (mutant) enzyme solution and different concentrations of soraphen A (0 $\mu$g/ml, 150 $\mu$g/ml, 1.5 $\mu$g/ml, 0.015 $\mu$g/ml). $^{14}$C-labeled $NaHCO_3$ is added at a concentration of 10 $\mu$Ci per sample with specific activities of 52.4 $\mu$Ci/$\mu$mol. The samples are brought to 200 $\mu$l with water, preincubated for 3 minutes at 30° C., and the reaction is started by addition of 0.5 mM acetyl-CoA. After 8 minutes the reaction is stopped by addtion of 50 $\mu$l 5N HCl. 200 $\mu$l of the sample are dried at 60° C. under nitrogen and dissolved in 300 $\mu$l water. 5 ml of scintillation solution is added and the remaining radioactivity is measured in a scintillation counter. As a control for unspecific incorpration of $H^{14}CO_3^-$ the reaction is performed without addition of acetyl-CoA. The results are then corrected for unspecific incorporation.

15.2. Spectrophotometric assay for acetyl-CoA carboxylase activity

In this method the byproduct of the acetyl-CoA carboxylase reaction ADP is measured. ADP and phosphoenolpyruvate are converted to pyruvate by pyruvate kinase which is then reduced to lactate by lactatedehydrogenase under oxidation of NADH. The oxidation rate of NADH can be quantitatively measured at 340 nm (Matsuhashi in: 'Methods of enzymology', 14:3–6).

The assay is perfomed in plastic cuvettes using the following reaction mixture: 50 mM Tris-HCl pH 8; 10 mM MgCl; 10 mM EDTA, 0.25 mM NADH; 3.75 nM ATP; 25 mM $KHCO_3$; 1.0 mM phosphoenolpyruvate; 0.6 mg BSA; 4 units pyruvate kinase; 4.5 units lactate dehydrogenase; 60 $\mu$l enzyme solution and optionally different concentrations of soraphen A (0 $\mu$g/ml, 150 $\mu$g/ml, 1.5 $\mu$g/ml, 0.015 $\mu$g/ml). Water is added to give a final volume of 0.8 ml. The reaction is started by addition of 0.1 $\mu$M acetyl-CoA. The $OD_{340}$ is monitored for the first 5 minutes after start of the reaction.

When this assay is used it has to be considered that copurified pyravatecarboxylase will disturb the assay and give a background of 15%.

What is claimed is:

1. An assay to identify inhibitors of soraphen A resistant acetyl-coenzyme A carboxylase, comprising
   (a) incubating a first sample of soraphen A resistant acetyl-coenzyme A carboxylase and its substrate in the absence of an inhibitor;
   (b) measuring reactivity of the acetyl-coenzyme A carboxylase in step (a);
   (c) incubating a second sample of soraphen A resistant acetyl-coenzyme A carboxylase and its substrate in the presence of a compound suspected to inhibit reactivity;
   (d) measuring reactivity of the acetyl-coenzyme A carboxylase in step (c);
   (e) comparing the reactivity of acetyl-coenzymeA carboxylase in step (b) and the reactivity of acetyl-coenzyme A carboxylase in step (d); and
   (f) identifying inhibitors causing a significant decrease in reactivity as compared to uninhibited reactivity.

2. An assay to identify inhibitors of soraphen A resistant fungal acetyl-coenzyme A carboxylase, comprising
   (a) growing a first culture of a fungus resistant to soraphen A in the absence of an inhibitor and recording its growth curve;
   (b) growing a second culture of a fungus resistant to soraphen A in the presence of a compound suspected to inhibit the reactivity of a soraphen A resistant acetyl-coenzyme A carboxylase and recording its growth curve;
   (c) comparing the growth curves recorded in steps (a) and (b), and
   (d) identifying inhibitors causing a reduction of the growth curve as compared to uninhibited growth.

* * * * *